United States Patent [19]

Timmins et al.

[11] Patent Number: 6,031,004
[45] Date of Patent: Feb. 29, 2000

[54] SALTS OF METFORMIN AND METHOD

[75] Inventors: Peter Timmins, Merseyside, United Kingdom; William J. Winter, Lebanon; Sushil K. Srivastava, Dayton, both of N.J.; Alison E. Bretnall, Chester, United Kingdom; Chenkou Wei, Princeton Junction; Gerald L. Powers, North Brunswick, both of N.J.

[73] Assignee: Bristol-Myers Squibb Company, Princeton, N.J.

[21] Appl. No.: 09/262,526

[22] Filed: Mar. 4, 1999

Related U.S. Application Data

[63] Continuation of application No. 08/986,586, Dec. 8, 1997.
[51] Int. Cl.$^7$ .................................................. A61K 31/155
[52] U.S. Cl. .................................................. 514/635
[58] Field of Search ............................... 514/635

[56] References Cited

U.S. PATENT DOCUMENTS 3,174,901   3/1965   Sterne .

FOREIGN PATENT DOCUMENTS

| 2037002 | 1/1996 | France . |
|---|---|---|
| 2320735 | 6/1996 | France . |
| 64008237 | 3/1995 | Japan . |
| WO97/17975 | 5/1997 | WIPO . |

*Primary Examiner*—Zohreh Fay
*Attorney, Agent, or Firm*—Burton Rodney

[57] ABSTRACT

Novel salts of the antidiabetic agent metformin acre provided which are metformin salts of dibasic acids (2:1 molar ratio), preferably metformin (2:1) fumarate and metformin (2:1) succinate, which may be employed alone or in combination with another antihyperglycemic agent such as glyburide, for treating diabetes. A method for treating diabetes employing the novel metformin salt by itself or in combination with another antidiabetic agent is also provided.

24 Claims, No Drawings

SALTS OF METFORMIN AND METHOD

This is a continuation of Ser. No. 08/986,586 filed Dec. 8, 1997.

FIELD OF THE INVENTION

The present invention relates to salts of the anti-diabetic agent metformin, and more particularly to metformin salts of dibasic acids, preferably dibasic organic carboxylic acids, optionally in combination with other anti-diabetic agent and to a method employing such salts or combinations for treating diabetes.

BACKGROUND OF THE INVENTION

The biguanide antihyperglycemic agent metformin is concurrently marketed in the U.S. in the form of its hydrochloride salt (Glucophage™, Bristol-Myers Squibb Company).

Metformin hydrochloride is a cohesive white powder which is highly soluble in water (>300 mg/ml at ambient temperature), has a hygroscopicity measured at 95% relative humidity /25° C. of greater than 20% moisture uptake at 6 hours, and a high compaction susceptibility. Accordingly, handling of metformin hydrochloride in a pharmaceutical manufacturing facility could present problems especially in high humidity environments. Furthermore, formulation of the metformin hydrochloride in a controlled release system is exceedingly difficult due, at least in part, to its extremely high water solubility.

The currently marketed metformin hydrochloride salt has a pronounced saline, bitter taste. Accordingly, it is usually marketed as a coated tablet where the coating is designed to mask any unpleasant taste. However, where the metformin hydrochloride salt is in the form of scored-divisible tablets, it will not usually have a coating or outer layer to mask the unpleasant taste.

Taste is of primary concern where the metformin hydrochloride is to be formulated as a chewable tablet or liquid indicated for children or adults who are not able to swallow tablets.

In such cases, the unpleasant taste of the hydrochloride salt could lead to compliance problems.

The prior art is replete with references disclosing metformin salts of various organic or inorganic acids in a 1:1 molar ratio of metformin:acid. Thus, for example, U.S. Pat. No. 3,174,901 discloses phosphate, sulfate, hydrobromide, salicylate, maleate, benzoate, succinate, ethanesulfonate, fumarate and glycolate salts of metformin;

U.S. Pat. No. 4,835,184 discloses the p-chlorophenoxyacetic acid salt of metformin;

French Patent Nos. 2320735 and 2037002 disclose the pamoate salt of metformin;

French Patent No. 2264539 and Japanese Patent No. 66008075 disclose the orotate salt of metformin;

French Patent No. 2275199 discloses the (4-chlorophenoxy) isobutyrate salt of metformin;

U.S. Pat. No. 4,080,472 discloses the clofibrate salt of metformin;

U.S. Pat. No. 3,957,853 discloses the acetylsalicylate salt of metformin;

French Patent No. 2220256 discloses the theophyllin-7-acetate salt of metformin;

German Patent Nos. 2357864 and 1967138 disclose the nicotinic acid salt of metformin;

U.S. Pat. No. 3,903,141 discloses the adamantoate salt of metformin;

Japanese Patent No. 69008566 discloses the zinc-chlorophyllin salt of metformin;

Japanese Patent No. 64008237 discloses hydroxy acid salts of metformin, including salts of hydroxy aliphatic dicarboxylic acids such as mesotartaric acid, tartaric acid, mesoxalic acids, and oxidized maleates;

Japanese Patent No. 63014942 discloses the tannic acid salt of metformin;

Japanese Patent Nos. 87005905 and 61022071 disclose the 3-methyl-pyrazole-5-carboxylic acid (or other 5-members hetercycle carboxylic acid) salt of metformin;

Romanian Patent No. 82052 discloses sulfamido aryloxy-alkyl carboxylic acid salts of metformin;

Soviet Union Patent No. 992512 discloses the trimethoxy benzoic acid salt of metformin;

U.S. Pat. No. 4,028,402 discloses the dichloroacetic acid salt of metformin.

U.S. Pat. No. 5,631,224 to Efendic et al issued May 20, 1997, discloses a combination of metformin with GLP-1(7-36) amide, or GLP-1(7-37) or a fragment thereof which retains GLP-1(7-37) activity.

DESCRIPTION OF THE INVENTION

In accordance with the present invention, novel salts of metformin are provided which retain equivalent antihyperglycemic activity to metformin hydrochloride, but which have improved handling properties as compared to metformin hydrochloride salt, including lower hygroscopicity and better flow properties as well as reduced compaction susceptibility and reduced corrosiveness such as to tablet tooling. The novel salts of the invention will also have improved taste properties as compared to the hydrochloride salt thus enhancing patient compliance, especially where the novel salts are in the form of scored tablets, chewable tablets or liquids.

In addition, the novel salts of metformin of the invention are significantly less soluble in water than the hydrochloride salt and thus provide the opportunity for formulating metformin in controlled release systems which require less polymer excipients to achieve a desired metformin release rate.

The novel metformin salts of the invention are metformin salts of dibasic acids wherein the molar ratio of metformin:dibasic acid is 2:1.

The dibasic acid forming the novel salt with metformin is preferably a dibasic organic carboxylic acid succinic acid and fumaric acid. Most preferred are the metformin (2:1) salt of succinic acid and the metformin (2:1) salt of fumaric acid.

The preferred metformin (2:1) fumarate salt of the invention is a free-flowing white crystalline solid which has a solubility in water at ambient temperature of 140 mg salt per ml water.

The preferred metformin (2:1) succinate salt of the invention is a free-flowing white powder which has a solubility in water at ambient temperature of 95 mg salt per ml water.

Moreover, metformin hydrochloride is a cohesive white powder which has a high solubility in water at ambient temperature of greater than 300 mg metformin per ml water.

The metformin (2:1) fumarate salt and metformin (2:1) succinate salt of the invention each has a low hygroscopicity measured at 95% relative humidity at 25° C. of less than 7% moisture uptake at 6 hours; while metformin hydrochloride has a high hygroscopicity measured at 95% relative humidity of greater than 20% moisture uptake at 6 hours.

Furthermore, the metformin (2:1) salts of the invention have reduced compaction susceptibility (tendency of the salt to compact under its own weight) as compared to the high compaction susceptibility of the metformin hydrochloride salt which could cause problems in bulk transport.

Accordingly, the novel metformin (2:1) salts of the invention with their lower hygroscopicity and improved flow properties and reduced compaction susceptibility, provide substantial and unexpected benefits over metformin hydrochloride in terms of handling during tabletting manufacture.

Surprisingly, it has also been found that the metformin (2:1) fumarate salt and the metformin (2:1) succinate salt have a substantially more tolerable taste as compared to the metformin hydrochloride salt. Accordingly, fumarate and succinate salts of the invention may be formulated as scored tablets, as well as chewable tablets or liquids without having an adverse effect on patient compliance.

The metformin (2:1) salts of dibasic acids of the invention are prepared employing conventional salt forming procedures. Thus, for example, the metformin base (which may be prepared from the hydrochloride using an ion-exchange column or other conventional technique) is dissolved in methanol or other suitable solvent and then admixed with a solution of the dibasic organic carboxylic acid, such as fumaric acid or succinic acid, in ethanol or other suitable solvent (in a 2:1 molar ratio metformin:dibasic acid). The desired salt crystallizes out and may be recovered by filtration, and dried to form a free flowing solid.

Still further in accordance with the invention, novel antihyperglycemic combinations are provided which include a metformin salt of a dibasic acid (2:1 molar ratio) in combination with another antihyperglycemic agent which may be administered orally or by injection.

The use of the metformin salt of the invention in combination with another anti-hyperglycemic agent produces anti-hyperglycemic results greater than that possible from each of these medicaments alone and greater than the combined additive anti-hyperglycemic effects produced by these medicaments.

The other antihyperglycemic agent may be an oral anti-hyperglycemic agent preferably a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide being preferred.

The metformin salt of the invention will be employed in a weight ratio to the sulfonyl urea in the range from about 300:1 to about 50:1, preferably from about 250:1 to about 75:1.

The oral antihyperglycemic agent may also be a glucosidase inhibitor such as acarbose (disclosed in U.S. Pat. No. 4,904,769) or miglitol (disclosed in U.S. Pat. No. 4,639,436).

The metformin salt of the invention will be employed in a weight ratio to the glucosidase inhibitor within the range from about 300:1 to about 2:1, preferably from about 200:1 to about 25:1.

The metformin salt of the invention may be employed in combination with a thiazolidinedione oral anti-diabetic agent (which has an insulin sensitivity effect in NIDDM patients) such as troglitazone (Warner-Lambert's Rezulin®, disclosed in U.S. Pat. No. 4,572,912), zorglitazone (SKB), pioglitazone (Takeda), Mitsubishi's MCC-555 (disclosed in U.S. Pat. No. 5,594,016) Glaxo-Welcome's GL-262570, englitazone (CP-68722, Pfizer) or darglitazone (CP-86325, Pfizer).

The metformin salt of the invention will be employed in a weight ratio to the thiazolidinedione in an amount within the range from about 75:1 to about 0.1:1, preferably from about 5:1 to about 0.5:1.

The novel metformin salt of the invention may also be employed in combination with a non-oral antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, orally, or by transdermal or buccal devices.

The novel metformin salts of the invention alone or in combination with another antihyper-glycemic agent may also be employed in combination with amylin.

In addition, in accordance with the present invention a method is provided for treating hyperglycemia including Type II diabetes (NIDDM) and/or Type I diabetes (IDDM) wherein a therapeutically effective amount of a metformin salt of a dibasic acid (2:1 molar ratio), optionally in combination with another antihyperglycemic agent, is administered to a patient in need of treatment.

Where present, the sulfonyl ureas, such as glyburide, glimepiride, glipyride, glipizide, chlorpropamide and gliclazide and the glucosidase inhibitors acarbose or miglitol may be employed in formulations, amounts and dosing as indicated in the Physician's Desk Reference.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The novel metformin salts of the present invention are potent anti-hyperglycemic agents at least equivalent to metformin hydrochloride and can be administered to various mammalian species, such as dogs, cats, humans, etc., in need of such treatment in the same manner as metforin hydrochloride. These metformin salts can be administered systemically, preferably orally.

The metformin salts of the invention alone or in combination with one or more oral antihyperglycemic agents can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms of the metformin (2:1) salt of the invention (whether by itself or with another antihyperglycemic agent) described above may be administered in amounts as described for metformin hydrochloride (Bristol-Myers Squibb Company's Glucophage®) as set out in the Physician's Desk Reference.

The combination of the metformin salt of the invention and the other antihyperglycemic agent may be formulated separately or, where possible, in a single formulation employing conventional formulation procedures.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tablet disintegrants in an amount within the range of from about 0.5 to about 10% and preferably from about 2 to about 8% by weight of the composition such as croscarmellose sodium, povidone, crospovidone, sodium starch glycolate, corn starch or microcrystalline cellulose as well as one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, antiadherents or silica flow conditioners or glidants, such as Syloid brand silicon dioxide as well as FD&C colors.

Tablets of the invention may also include a coating layer which may comprise from 0 to about 15% by weight of the tablet composition. The coating layer which is applied over the tablet core may comprise any conventional coating formulations and will include one or more film-formers or binders, such as a hydrophilic polymer like hydroxypropylmethyl cellulose and a hydrophobic polymer like ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

A preferred tablet composition of the invention will include from about 90 to about 97.5% by weight metformin (2:1) salt from about 2 to about 8% by weight providone, and from about 0.5 to about 2% by weight magnesium stearate.

The pharmaceutical composition of the invention may be prepared as follows. A mixture of the medicament and a fraction (less than 50%) of the filler where present (such as lactose), with or without color, are mixed together and passed through a #12 to #40 mesh screen. Filler-binder where present (such as microcrystalline cellulose), disintegrant (such as providone) are added and mixed. Lubricant (such as magnesium stearate) is added with mixing until a homogeneous mixture is obtained.

The resulting mixture may then be compressed into tablets of up to 2 grams in size.

Where desired, the tablets of the invention may be formulated by a wet granulation techniques as disclosed in U.S. Pat. No. 5,030,447 which is incorporated herein by reference.

The following examples represent preferred embodiments of the invention.

EXAMPLE 1

Preparation of Metformin (2:1) Fumarate

Metformin base (8.71 moles) (prepared from the hydrochloride salt via an ion-exchange column) was dissolved in methanol/$H_2O$ [5:1]. With stirring, a solution of fumaric acid (4.05 moles) in ethanol was added over a period of one hour under a nitrogen atmosphere at ambient temperature (~20° C.). Crystallization began to occur immediately. After stirring the slurry for one hour at ambient temperature, the product was filtered off, washed with ethanol and dried under vacuum to afford the metformin (2:1) fumarate salt as a free-flowing white crystalline solid in 72 M% yield and melting point of 247–249° C.

The resulting metformin (2:1) fumarate salt had a solubility in water (mg/ml) of 140, a hygroscopicity measured at 95% relative humidity/25° C. of less than 7% moisture uptake at 6 hours, and a low compaction susceptibility. Tabletting of the metformin (2:1) fumarate salt resulted in reduced corrosion of tablet tooling equipment as compared with the corresponding hydrochloride salt.

EXAMPLE 2

Preparation of Metformin (2:1) Succinate

Metformin base (8.95 moles) (prepared from the hydrochloride salt via an ion-exchange column) was dissolved in methanol/$H_2O$ [5:1]. With stirring, a solution of succinic acid (4.42 moles) in ethanol was added over one hour under a nitrogen atmosphere at ambient temperature (~20° C.). Crystallization of the salt commenced shortly after addition of the succinic acid solution. After stirring the slurry for an hour at ambient temperature, the product was filtered off, washed with ethanol and dried under vacuum to form the metformin (2:1) succinate salt as a free flowing white crystalline solid in 89 M % yield and melting point of 246–247° C.

The resulting metformin (2:1) succinate salt had a solubility in water (mg/ml) of 95, a hygroscopicity measured at 95% relative humidity/25° C. of less than 1% moisture uptake at 30 minutes, and a low compaction susceptibility. Tabletting of the metformin (2:1) fumarate salt resulted in reduced corrosion of tablet tooling equipment as compared with the corresponding hydrochloride salt.

EXAMPLE 3

Preparation of Tablets Containing Metformin (2:1) Fumarate

Tablets of the following formulation were prepared as described below.

| Ingredient | Amount per tablet (mg) |
|---|---|
| Metformin (2:1) fumarate | 600.0 mg |
| Microcrystalline cellulose NF | 80.0 mg |
| Croscarmellose sodium NF | 45.0 mg |
| Povidone USP | 15.0 mg |
| Magnesium Stearate NF | 8.0 mg |

In a planetary mixer metformin (2:1) fumarate was blended with half the microcrystalline cellulose and with the croscarmellose sodium. The povidone USP was dissolved in a suitable quantity of purified water and this solution was used to wet granulate the drug-excipient mixture. The granules were dried in an oven at 60° C. to a moisture content of 1.5–2.5% w/w. In a V-cone blender the granules were mixed with the remaining microcrystalline cellulose and then with the magnesium stearate. The resulting mix was compressed into tablets using suitable capsule shaped tooling.

This formulation does not require introduction of additional moisture immediately prior to compression as is the case with metformin hydrochloride formulations in order to ensure trouble free tabletting.

The metformin fumarate salt has a less intense taste than metformin hydrochloride which means film coating of the final metformin fumarate tablet is not necessary.

EXAMPLE 4

Preparation of Tablets Containing Metformin (2:1) Succinate

Tablets of the following formulation are prepared as described below.

| Ingredient | Amount per tablet (mg) |
|---|---|
| Metformin (2:1) succinate | 600.0 mg |
| Microcrystalline cellulose NF | 80.0 mg |
| Croscarmellose sodium NF | 45.0 mg |
| Hydroxypropylmethyl cellulose (5 cps) (HPMC) USP | 15.0 mg |
| Magnesium Stearate NF | 8.0 mg |

In a planetary mixer the metformin (2:1) succinate is blended with half the microcrystalline cellulose and with the croscarmellose sodium. The HPMC USP is dispersed in a suitable quantity of purified water and this mixture is used to wet granulate the drug-excipient mixture. The granules are dried in an oven at 60° C. to a moisture content of 1.5–2.5% w/w. In a V-cone blender the granules are mixed with the remaining microcrystalline cellulose and then with the magnesium stearate. The resulting mix is compressed into tablets using suitable capsule shaped tooling.

This formulation does not require introduction of additional moisture immediately prior to compression as is the case with metformin hydrochloride formulations in order to ensure trouble free tabletting.

EXAMPLE 5

Preparation of Tablets Containing Metformin (2:1) Fumarate and Glyburide

Tablets of the following formulation are prepared as described below.

| Ingredient | Amount per tablet (mg) |
|---|---|
| Metformin (2:1) fumarate | 600.0 mg |
| Glyburide | 5.0 mg |
| Microcrystalline cellulose NF | 80.0 mg |
| Croscarmellose sodium NF | 45.0 mg |
| Povidone USP | 15.0 mg |
| Magnesium Stearate NF | 8.0 mg |

In a planetary mixer metformin (2:1) fumarate is blended with half the microcrystalline cellulose and with the croscarmellose sodium. The povidone USP is dissolved in a suitable quantity of purified water and this solution is used to wet granulate the drug-excipient mixture. The granules are dried in an oven at 60° C. to a moisture content of 1.5–2.5% w/w. In a V-cone blender the granules are mixed with the remaining microcrystalline cellulose and then with the magnesium stearate. The resulting mix is compressed into tablets using suitable capsule shaped tooling.

This formulation does not require introduction of additional moisture immediately prior to compression as is the case with metformin hydrochloride formulations in order to ensure trouble free tabletting, and the less intense taste of the fumarate salt means film coating of the final tablet may not be necessary.

EXAMPLE 6

Preparation of Tablets Containing Metformin (2:1) Succinate and Glyburide

Tablets of the following formulations are prepared as described below.

| Ingredient | Amount per tablet (mg) |
|---|---|
| Metformin (2:1) succinate | 600.0 mg |
| Glyburide | 5.0 mg |
| Microcrystalline cellulose NF | 80.0 mg |
| Croscarmellose sodium NF | 45.0 mg |
| Hydroxypropylmethyl cellulose (5 cps) USP | 15.0 mg |
| Magnesium Stearate NF | 8.0 mg |

In a planetary mixer metformin (2:1) succinate and glyburide are blended with half the microcrystalline cellulose and with the croscarmellose sodium. The HPMC USP is dissolved in a suitable quantity of purified water and this solution is used to wet granulate the drug-excipient mixture. The granules are dried in an oven at 60° C. to a moisture content of 1.5–2.5% w/w. In a V-cone blender the granules are mixed with the remaining microcrystalline cellulose and then with the magnesium stearate. The resulting mix is compressed into tablets using suitable capsule shaped tooling.

This formulation does not require introduction of additional moisture immediately prior to compression as is the case with metformin hydrochloride formulations in order to ensure trouble free tabletting.

EXAMPLE 7

Preparation of Tablets Containing Metformin (2:1) Fumarate and Glipizide

Tablets of the following formulations are prepared as described below.

| Ingredient | Amount per tablet (mg) |
| --- | --- |
| Metformin (2:1) fumarate | 600.0 mg |
| Glipizide | 5.0 mg |
| Microcrystalline cellulose NF | 80.0 mg |
| Croscarmellose sodium NF | 45.0 mg |
| Povidone USP | 15.0 mg |
| Magnesium Stearate NF | 8.0 mg |

In a planetary mixer metformin (2:1) fumarate and glipizide are blended with half the microcrystalline cellulose and with the croscarmellose sodium. The povidone USP is dissolved in a suitable quantity of purified water and this solution is used to wet granulate the drug-excipient mixture. The granules are dried in an oven at 60° C. to a moisture content of 1.5–2.5% w/w. In a V-cone blender the granules are mixed with the remaining microcrystalline cellulose and then with the magnesium stearate. The resulting mix is compressed into tablets using suitable capsule shaped tooling.

This formulation does not require introduction of additional moisture immediately prior to compression as is the case with metformin hydrochloride formulations in order to ensure trouble free tabletting.

EXAMPLE 8

Preparation of Tablets Containing Metformin (2:1) Succinate and Glipizide

Tablets of the following formulations were prepared as described below.

| Ingredient | Amount per tablet (mg) |
| --- | --- |
| Metformin (2:1) succinate | 600.0 mg |
| Glipizide | 5.0 mg |
| Microcrystalline cellulose NF | 80.0 mg |
| Croscarmellose sodium NF | 45.0 mg |
| Hydroxypropyl methyl cellulose (5 cps) USP | 15.0 mg |
| Magnesium Stearate NF | 8.0 mg |

In a planetary mixer metformin (2:1) succinate and glipizide are blended with half the microcrystalline cellulose and with the croscarmellose sodium. The HPMC USP is dissolved in a suitable quantity of purified water and this mixture is used to wet granulate the drug-excipient mixture. The granules are dried in an oven at 60° C. to a moisture content of 1.5–2.5% w/w. In a V-cone blender the granules are mixed with the remaining microcrystalline cellulose and then with the magnesium stearate. The resulting mix is compressed into tablets using suitable capsule shaped tooling.

This formulation does not require introduction of additional moisture immediately prior to compression as is the case with metformin hydrochloride formulations in order to ensure trouble free tabletting.

EXAMPLE 9

Preparation of Chewable Tablets Containing Metformin (2:1) Fumarate Salt

Chewable tablets of the following formulation are prepared as described below.

| Ingredient | Amount per tablet (mg) |
| --- | --- |
| Metformin (2:1) succinate | 600.0 mg |
| Xylitol | 450.0 mg |
| Flavor, grape | 0.5 mg |
| Flavor, spice | 0.5 mg |
| Magnesium Stearate NF | 10.0 mg |

The metformin (2:1) fumarate is passed through a suitable wire mesh screen (600 micron aperture). The flavor ingredients are blended with the pre-screened xylitol and the resulting mix is added to the metformin (2:1) fumarate in a V-cone blender. The mixture is mixed for ten minutes. The magnesium stearate is added to the contents of the V-cone blender, passing the magnesium stearate through a 425 micron aperture screen. The mix is mixed for 5 minutes and compressed into flat faced bevel edged tablets using suitable tooling.

EXAMPLE 10

Preparation of Chewable Formulation of Metformin (2:1) Succinate Salt

Chewable tablets of the following formulation are prepared as described below.

| Ingredient | Amount per tablet (mg) |
| --- | --- |
| Metformin (2:1) succinate | 600.0 mg |
| Xylitol | 450.0 mg |
| Flavor, raspberry | 0.5 mg |
| Magnesium Stearate NF | 10.0 mg |

The metformin (2:1) succinate is passed through a suitable wire mesh screen (600 micron aperture). The flavor ingredient is blended with the pre-screened xylitol and the resulting mix is added to the metformin (2:1) succinate in a V-cone blender. The mixture is mixed for ten minutes. The magnesium stearate is added to the contents of the V-cone blender, passing the magnesium stearate through a 425 micron aperture screen. The mix is mixed for 5 minutes and compressed into flat faced bevel edged tablets using suitable tooling.

EXAMPLE 11

The following experiment was carried out to determine moisture sorption/desorption profiles of metformin (2:1) fumarate salt and metformin (2:1) succinate salt compared to the moisture uptake properties of metformin hydrochloride salt.

The procedure employed was as follows:

The hygroscopicity of metformin salts was assessed by Dynamic Vapour Sorption (DVS), a means of rapidly assessing sample moisture uptake properties. Approximately 5 mg of sample is placed on a suitable microbalance sample pan in a controlled temperature environment (held at 30° C.) and which is suitably tared against a separate blank pan. Both chambers are subjected to a controlled program of incremental increase in RH from 0% to 95% by means of a moisture saturated air/dry nitrogen variable mixture gas stream. The weight increase of sample at each condition is recorded until a defined minimal rate of mass change is reached or a specified time period for equilibrium exceeded.

A reverse cycle from 95% to 0% is performed immediately, allowing an absorption and desorption profile to be generated and from which the hygroscopicity was determined.

The following moisture uptake at 95% relative humidity/25° C. is observed.

| Time | % moisture uptake |
|---|---|
| (1) metformin hydrochloride | |
| 30 min | 1.2% |
| 70 min | 3.3% |
| 3 hours | 10.0% |
| 6 hours | 20.1% |
| (did not reach equilibrium) | |
| (2) metformin (2:1) fumarate | |
| 30 min | 1.0% |
| 70 min | 2.0% |
| 3 hours | 4.1% |
| 6 hours | 6.6% |
| (did not reach equilibrium) | |
| (3) metformin (2:1) succinate | |
| 30 min | 0.27% |
| (reach equilibrium) | |

In summary, the degree of moisture uptake for the salts tested were found to occur in the following rank order:
  (1) metformin hydrochloride salt: 20% moisture content after 6 hours at 95% relative humidity at 25° C.
  (2) metformin (2:1) fumarate salt: 6.6% moisture after 6 hours at 95% relative humidity at 25° C.
  (3) metformin (2:1) succinate: 0.27% equilibrium moisture content after 30 minutes at 95% relative humidity at 25° C.

From the above results, it is seen that metformin hydrochloride salt absorbs substantially greater amounts of moisture as compared to the metformin (2:1) fumarate salt of the invention and the metformin (2:1) succinate salt of the invention. Accordingly, the metformin (2:1) salts of the invention will have improved handling properties during tabletting as compared to the metformin hydrochloride salt.

What is claimed is:

1. A metformin salt of a dibasic acid in a molar ratio of 2 moles metformin to 1 mole dibasic acid, having a solubility in water (mg/ml) at ambient temperature of less than about 150 mg/ml. which is metformin (2:1) fumarate or metformin (2:1) succinate.

2. The metformin salt as defined in claim 1 which is metformin (2:1) fumarate.

3. The metformin salt as defined in claim 1 which is metformin (2:1) succinate.

4. The metformin salt as defined in claim 1 in the form of free flowing granules having a hygroscopicity measured at 95% relative humidity, 20° C. of less than 7% moisture uptake at 6 hours.

5. A pharmaceutical composition comprising a metformin salt as defined in claim 1 and a pharmaceutically acceptable carrier therefor.

6. The pharmaceutical composition as defined in claim 5 in the form of a tablet or capsule.

7. The pharmaceutical composition as defined in claim 5 further including another antihyperglycemic agent.

8. The pharmaceutical composition as defined in claim 7 wherein the other antihyperglycemic agent is glyburide or glipizide.

9. A method for treating hyperglycemia which comprises administering to a patient in need of treatment a therapeutically effective amount of a metformin salt as defined in claim 1.

10. The method as defined in claim 9 wherein the metformin salt is administered with a therapeutically effective amount of another antihyperglycemic agent.

11. The method as defined in claim 10 wherein the other antihyperglycemic agent is glyburide or glipizide.

12. A combination of a metformin salt of a dibasic acid in a molar ratio of 2 moles metformin to 1 mole dibasic acid, which metformin salt is the metformin (2:1) fumarate or the metformin (2:1) succinate, and another antihyperglycemic agent.

13. The combination as defined in claim 12 wherein the metformin salt is metformin (2:1) fumarate.

14. The combination as defined in claim 12 wherein the other antihyperglycemic agent is a sulfonyl urea, a glucosidase inhibitor, a thiazolidinedione, a GLP-1 peptide, and/or insulin.

15. The combination ad defined in claim 14 wherein the antihyperglycemic agent is glyburide, glipizide, glimepiride, acarbose, miglitol, troglitazone or insulin.

16. The combination as defined in claim 12 which is metformin (2:1) fumarate or metformin (2:1) succinate, and glyburide or glipizide.

17. A metformin salt of a dibasic acid in a molar ratio of 2 moles metformin to 1 mole dibasic acid, which is metformin (2:1) fumarate.

18. A metformin salt of a dibasic acid in a molar ratio of 2 moles metformin to 1 mole dibasic acid, which is metformin (2:1) succinate.

19. A pharmaceutical composition comprising metformin (2:1) fumarate and a pharmaceutically acceptable carrier therefor.

20. A combination comprising metformin (2:1) fumarate and glyburide.

21. A combination comprising metformin (2:1) fumarate and glipizide.

22. The pharmaceutical composition as defined in claim 9 in the form of a single dosage form.

23. The pharmaceutical composition as defined in claim 22 wherein the combination is incorporated in a tablet or capsule.

24. A pharmaceutical composition comprising metformin (2:1) fumarate and glipizide, and a pharmaceutically acceptable carrier therefor.

* * * * *